United States Patent [19]

Maneglier et al.

[11] Patent Number: 5,340,574
[45] Date of Patent: Aug. 23, 1994

[54] STABILIZED NON-GLYCOSYLATED RECOMBINANT HUMAN IL2 IN REDUCED FORM COMPOSITIONS

[75] Inventors: Bruno Maneglier, Paris; Bernard Voncken, Fosses sur Villiers, both of France

[73] Assignee: Roussel-UCLAF, France

[21] Appl. No.: 989,230

[22] Filed: Dec. 11, 1992

[30] Foreign Application Priority Data

Dec. 12, 1991 [FR] France ............... 91-15418

[51] Int. Cl.$^5$ .............................................. A61K 45/05
[52] U.S. Cl. .................................. 424/85.2; 514/12; 514/21
[58] Field of Search ................ 424/85.2; 514/12, 21

[56] References Cited

U.S. PATENT DOCUMENTS

| | | | |
|---|---|---|---|
| 4,572,798 | 2/1986 | Koths et al. | 530/351 |
| 4,645,830 | 2/1987 | Yasushi et al. | 530/351 |
| 4,748,234 | 5/1988 | Dorin et al. | 530/351 X |
| 4,780,313 | 10/1988 | Koichiro et al. | 424/88 |
| 4,812,557 | 3/1989 | Yasushi et al. | 530/351 |
| 4,816,440 | 3/1989 | Thomson | 514/12 |
| 4,863,726 | 9/1989 | Stevens et al. | 424/85.2 |
| 4,902,502 | 2/1990 | Nitecki et al. | 424/85.1 |
| 4,904,467 | 2/1990 | Schwulera | 424/85.2 |
| 4,931,543 | 6/1990 | Halenbeck et al. | 530/351 |
| 4,931,544 | 6/1990 | Katre et al. | 530/351 |
| 5,004,605 | 4/1991 | Hershenson et al. | 424/85.6 |
| 5,037,644 | 8/1991 | Shaked et al. | 424/85.2 |
| 5,078,997 | 1/1992 | Hora et al. | 424/85.2 |
| 5,204,094 | 4/1993 | Brandely et al. | 424/85.2 |

FOREIGN PATENT DOCUMENTS

| | | |
|---|---|---|
| 0229016 | 7/1987 | European Pat. Off. |
| 0231132 | 8/1987 | European Pat. Off. |
| 0251001 | 1/1988 | Fed. Rep. of Germany |
| 0353150 | 1/1990 | France |
| 0452598 | 10/1991 | France |
| 8504328 | 10/1985 | PCT Int'l Appl. |

OTHER PUBLICATIONS

Wang et al., "Parenteral Formulations of Proteins & Peptides ...", Jour. of Parenteral Science & Technology, vol. 42, No. 25, (1988) pp. S3–S26.

*Primary Examiner*—Michael G. Wityshyn
*Assistant Examiner*—C. Sayala
*Attorney, Agent, or Firm*—Bierman and Muserlian

[57] ABSTRACT

A stabilized composition comprising an effective amount of non-glycosylated recombinant human IL2 in reduced form, citric acid, mannitol and a preservative effective amount of a mixture of dextran and mono-calcium and disodium ethylenediamine tetraacetate, particularly in lyophilized form.

13 Claims, No Drawings

STABILIZED NON-GLYCOSYLATED RECOMBINANT HUMAN IL2 IN REDUCED FORM COMPOSITIONS

STATE OF THE ART

Natural human IL2 which is a lymphokine stimulating the proliferation of activated T cells has three cysteines located in positions 58,105 and 125 of the sequence of the 133 amino acids of the protein. In the natural molecule, cysteines 58 and 105 are joined by a disulfide bridge, while cysteine 125 has a free sulfhydryl group (Robb et al, Proc. Natl. Acad, Sci. (1984), Vol. 81, pp. 6486–6490). Preparation processes for human IL2, alleles or derivatives by recombinant DNA technology are also described, in European Patent No. EP 091,539.

The obtaining of a high purity natural or recombinant IL2 preparation necessary for use as a medicament generally leads to instability of its biological activity, particularly during prolonged storage in liquid form, in a frozen state or in a lyophilized form. Stabilizers of the biological activity of pure IL2 are known and are used such as polyethylene glycols, reducing agents such as dithiothreitol and mercaptoethanol or human serum albumin.

Thus, European patent application No. EP 0,251,001 describes a composition of pure natural IL2, the biological activity of which is stabilized for prolonged preservation in solution, in a frozen state or in a lyophilized form by the addition of albumins or globulins, optionally combined with other agents such as sugar-alcohols, sugar monomers or polymers such as hydroxystarch or a dextran.

Moreover, a new recombinant human IL2, non-glycosylated (r-hIL2), in reduced form having a biological activity at least equal to $0.5 \times 10^7$ U/mg and pharmaceutical compositions containing it for use as a medicament are described in European patent application EP 0,353,150. IL2 in reduced form means an IL2 in which the 3 cysteines in positions 58, 105 and 125 contain a free sulfhydryl group and which has a biological activity comparable to that of the corresponding oxidized IL2 containing the disulfide bridge in position 58–105. The determination of the sulfhydryl groups, for example by spectrophotometry with dithiopyridine, and the usual determination of the biological activity by measuring the proliferation of the CTLL-2 murine cell lines, are indicated in Patent application No. EP 0,353,150.

An example is given of a lyophilized pharmaceutical composition of the reduced r-hIL2 mentioned above containing citric acid and mannitol and suitable for injection into a patient, as well as an example of a liquid composition more particularly suitable for administration by continuous perfusion.

Generally, the prolonged preservation of pharmaceutical compositions containing a pure protein as active ingredient and intended to be used as medicaments is a constraint which is difficult to avoid. But such a storage is usually accompanied by a degradation which leads to a loss of the biological activity of the protein for various reasons such as physical modifications, for example the formation of dimers or aggregates, or such as chemical modifications, for example oxidation or deamidation. Therefore, the stability of the composition containing the therapeutic protein over relatively long periods of time, preferably for one year, at a suitable temperature, preferably at about $+5°$ C., is generally required. The obtaining of such a stability always requires the addition of stabilizers which differ generally according to the protein concerned.

The need for improved stability of pharmaceutical compositions relates in particular to the above compositions of reduced recombinant IL2 and more particularly, the composition of the latter in liquid or lyophilized form intended to be administered to patients.

The above liquid or lyophilized compositions of reduced r-hIL2 which are described in Patent application EP 0,353,150 have a suitable biological activity stability under preservation, particularly in the absence of albumin, unlike the known compositions of natural or recombinant IL2 which contain the disulfide bridge in position 58–105 and which generally have an insufficient stability of this activity.

However, the formation of the above reduced r-hIL2 dimer can be observed by electrophoresis on polyacrylamide gel (SDS-PAGE), particularly during preservation at different temperatures of lyophilized compositions, without however being accompanied by a significant decrease in the biological activity shown. Furthermore, the absence of albumin as stabilizer in the above compositions of reduced r-hIL2 allows their stability to be monitored using spectrophotometric detection, for example at 280 nm, after reverse phase liquid chromatography (called RP-HPLC) which reveals the possible formation of impurities at the expense of the IL2, depending on the duration of preservation and the preservation temperature, without however being accompanied by a decrease in biological activity.

Although the dimer formation or the formation of impurities detected by RP-HPLC, in the above case of reduced r-hIL2, is not accompanied by a decrease in the biological activity as measured in vitro, such formations could demonstrate the disadvantage of allowing the development of antigenic reactions during prolonged administration to a patient.

OBJECTS OF THE INVENTION

It is an object of the invention to provide stabilized compositions containing non-glycosated recombinant IL2 in reduced form.

It is another object of the invention to provide a novel method of stabilizing compositions of non-glycosated recombinant IL2 in reduced form.

These and other objects and advantages of the invention will become obvious from the following detailed description.

THE INVENTION

The composition of the invention is a stabilized composition comprising an effective amount of non-glycosylated recombinant human IL2 in reduced form, citric acid, mannitol and a preservative effective amount of a mixture of dextran and mono-calcium and disodium ethylenediamine tetraacetate. The compositions lack albumin or any other UV absorbent agents in the field of protein absorption, as well as by the essential absence of IL2 dimer formation during prolonged preservation, particularly in the lyophilized state, and are suitable for use as medicaments for patients. The essential absence of dimer formation means that the dimer content during storage varies by a percentage less than or equal to 2%.

Unexpectedly, the improvement of the stability of the above compositions of reduced r-hIL2 under preservation, particularly in the essential absence of IL2 dimer formation as defined above is obtained by the simultaneous addition of dextran and monocalcium and disodium salt of ethylenediaminetetraacetic acid (called EDTA calcium salt) to solutions of reduced r-hIL2 containing citric acid and mannitol.

Dextran is a branched polymer of glucose, the different fractions of which define the specific average molecular weights and which are used particularly as a blood plasma substitute in human therapeutics. EDTA calcium salt is a chelating agent suitable for pharmaceutical use.

The non-glycosylated recombinant human IL2 in reduced form to which the invention relates has a biological activity at least equal to $0.5 \times 10^7$ U/mg, preferably equal to about $1 \times 10^7$ U/mg, according to the determination test indicated above. Improvement of the stability of the pharmaceutical compositions is observed on preservation of compositions containing the reduced IL2 defined above, citric acid and mannitol by the addition of a dextran and EDTA calcium salt followed by lyophilization, then storage for prolonged lengths of time at different temperatures. The improvement of the stability relates to the physical and chemical stability of the reduced r-hIL2 which can be monitored using analytical methods, for example by SDS-PAGE and by RP-HPLC respectively the operating conditions of which are given further on.

Particularly, the invention relates to a pharmaceutical composition the non-glycosylated recombinant human IL2 in reduced form characterized in that the dextran has an average molecular weight of about 40,000 to 110,000 and preferably about 70,000. Commercial dextrans are used, for example dextran 40, dextran 70 or dextran 110 which corresponds to dextran fractions having average molecular weights of about 40,000, 70,000 and 110,000 respectively, preferably dextran 70 which has an average molecular weight of about 70,000.

Preferred compositions of non-glycosylated recombinant human IL2 in reduced form are those in which the weight ratio of dextran:IL2 is about 20:1 to about 80:1 and especially in a ratio of about 40:1.

The weight of reduced r-hIL2 is expressed in mg of protein measured in the usual way by the RP-HPLC method. For example, a lyophilized composition containing 1 mg of the above reduced r-hIL2 is stabilized by the addition of about 20 to 80 mg of dextran, preferably about 40 mg. Preferably, the composition of non-glycosylated human IL2 in reduced form has a weight ratio of IL2:citric acid:mannitol:dextran:EDTA calcium salt of about 1: 10:50:40:0.01, for example, a lyophilized composition of 1 mg of the above reduced r-hIL2, 10 mg of citric acid and 50 mg of mannitol is stabilized by the addition of about 40 mg of dextran and about 10 micrograms of EDTA calcium salt.

The stabilized composition of non-glycosylated recombinant human IL2 in reduced form of the invention is characterized in that it is essentially free from IL2 dimer. By essentially free from IL2 dimer is meant that the IL2 composition contains an IL2 dimer content less than or equal to 2% at most.

The process for the preparation of a stabilized, lyophilized composition of non-glycosylated recombinant human IL2 in reduced form comprises lyophilizing a solution of a dextran, EDTA calcium salt and mannitol after adding an aqueous solution of IL2 containing citric acid.

The method of stabilizing a composition containing non-glycosylated recombinant human IL2 in reduced form, citric acid and mannitol comprises incorporating into said composition an amount of a mixture of dextran and calcium ethylenediamine tetraacetate sufficient to stabilize the composition.

In the following examples, there are described several preferred embodiments to illustrate the invention. However, it is to be understood that the invention is not intended to be limited to the specific embodiments.

EXAMPLE 1

Stabilized Pharmaceutical Composition of Reduced r-hIL2 for Injection 990 ml of an aqueous solution of 88 g of dextran 70, 0.022 g of EDTA calcium salt and 110 g of mannitol were added to 1210 ml of an aqueous solution of 2 mg/ml of reduced r-hIL2 and 18.2 mg/ml of citric acid as described in Patent application EP 0,353,150. The solution was filtered through a membrane with 0.22 micron diameter pores. After sterile distribution of 1 ml of the homogeneous solution into flasks, then lyophilization, the dosage flasks were sealed under a nitrogen atmosphere and could be preserved before use at a temperature of about 4° C. for at least one year.

The above lyophilized compositions had the following formula;

| | |
|---|---|
| reduced IL2 | about 1 mg |
| citric acid | 10 mg |
| mannitol | 50 mg |
| dextran 70 | 40 mg |
| EDTA calcium salt | 0.01 mg |

The compositions were suitable for injection in the patient after dissolution of the contents by injection of 1 ml of sterile distilled water, as well as for continuous perfusion after the introduction of the previously reconstituted solution into a Viaflex ® container containing 500 ml of solute for 5% glucose Travenol ® perfusion.

EXAMPLE 2

Stabilization of the Reduced r-hIL2 by Dextran and EDTA Calcium Salt

1—Analytical Methods a) Analysis by RP-HPLC

The possible formation of impurities during the preservation of reduced r-hIL2 compositions as well as the determination of the reduced IL2 expressed in mg of protein were evaluated by analytical RP-HPLC on a C4 VYDAC column (0.46×25 cm) 300 A, 5 microns, at a rate of 1 ml/min, with a linear gradient of acetonitrile varying from 0 to 30% over 5 minutes then from 30 to 73% over 20 minutes, containing 0.1% of trifluoroacetic acid and with a spectrophotometric detection at 280 or 220 nm.

b) SDS-PAGE

The possible formation of IL2 dimer was evaluated by electrophoresis on a gel with a 20% concentration of acrylamide. The sample was heated beforehand for 2 minutes at 100° C. in a denaturing buffer with 3% SDS and 5% mercaptoethanol. The migration was carried out with a 0.565% SDS buffer and followed by staining with silver. An apparent molecular weight of about 15.5 Kda for the reduced r-hIL2 and an apparent molecular weight of about 31 Kda for the dimer were determined.

c) Biological activity

It was determined by measuring the proliferation of the leukemic cell lines of CTLL-2 mice with the tetrazolium calorimetric test (Mossmann T. et al, J. Immunol. Meth. (1983) Vol. 65 p. 55–63).

2—Chemical Stabilization of the Reduced r-hIL2 by Dextran and EDTA Calcium Salt

The chemical stabilization of r-hIL2 by different dextrans in combination with EDTA calcium salt was studied at a temperature of 37° C. which allowed possible chemical modifications of the protein to be accelerated and a study to be carried out over relatively short periods of time. The study was carried out starting with a solution of reduced r-hIL2 containing citric acid to which a solution containing EDTA calcium salt, mannitol and respectively one of the dextrans to be studied was added under a nitrogen atmosphere. The solution was lyophilized after distribution of 1 ml into dosage flasks which were then kept at 37° C. for variable lengths of time over a period of one month. Control flasks without dextran and without EDTA calcium salt were placed simultaneously at 37° C. The content of each flask was then taken up in 1 ml of distilled water and analyzed by RP-HPLC.

The dosage flasks which were subjected to a stability test at 37° C. had the following formula:

| | |
|---|---|
| reduced IL2 | 0.55 mg |
| citric acid | 5 mg |
| mannitol | 50 mg |
| dextran | 40 mg |
| EDTA calcium salt | 0.01 mg |

The dextrans T 40, T 70 and T 110 marketed by Pharmacia were tested respectively. The following results were obtained:

| | Preservation at 37° C. Percentage of impurities measured by RP-HPLC | | | |
|---|---|---|---|---|
| Dextran | t = 0 | t = 8d | t = 15d | t = 30 |
| — | 2.64 | n.i. | n.i. | n.i. |
| Dextran 40 | 3.17 | 3.65 | 4.35 | 5.18 |
| Dextran 70 | 3.16 | 4.14 | 4.12 | 5.57 |
| Dextran 110 | 2.98 | 3.54 | 3.51 | 4.53 |

At a dose of 40 mg of dextran, a ratio by weight of IL2:dextran of about 80, the different types of average molecular weight of the dextrans studied had a comparable and remarkable effect on the chemical stability of the reduced r-hIL2 at 37° C., whereas in the absence of dextran and EDTA calcium salt, the quantity of impurities formed make the RP-HPLC non-interpretable (n.i.) for a preservation period of only 8 days. The influence of the concentration of dextran 70 was tested at doses of 10 and 20 respectively in comparison with the does of 40 mg as previously. The following results were obtained:

| | Preservation at 37° C. Percentage of impurities measured by RP-HPLC | |
|---|---|---|
| Dextran 70 | t = 0 | t = 30d |
| — | 2.64 | n.i. |
| 10 mg | | 8.41 |
| 20 mg | | 5.81 |
| 40 mg | | 4.13 |

An effect on the chemical stability of the reduced r-hIL2 was observed with dextran, already noticeable at the smallest dose which corresponds to a ratio by weight of IL2:dextran of about 1:20.

3—Physical Stabilization of the Reduced r-hIL2 by Dextran and EDTA Calcium Salt

The physical stabilization of the reduced r-hIL2 by dextran 70 in combination with EDTA calcium salt was studied during long-term preservation comprised between one month and one year at temperatures of $-20°$ C., $+2°/+8°$ C., ambient temperature (about $20°\pm5°$ C.) and 37° C. respectively. The study was carried out starting with the formula of Example 1. Control flasks without dextran and without EDTA calcium salt were placed simultaneously under the same storage conditions. The content of each flask was taken up in 1 ml of denaturing buffer indicated above and analyzed by SDS-PAGE. The percentage of dimer was determined. The biological activity was also determined on flasks having the same formula with dextran and EDTA calcium salt and kept under the same temperature conditions. The following results were obtained.

| Preservation | | IL2 dimer % (SDS-PAGE) | | $10^7$ IU/flask |
|---|---|---|---|---|
| Temperature °C. | Duration (months) | Dextran/ EDTA formula | control formula | Dextran/ EDTA formula |
| −20 | 1 | 1 | 1.5 | 1.15 |
| | 3 | 1 | 1 | |
| | 6 | 1 | 0.8 | 1.11 |
| | 9 | 1 | 1 | |
| | 12 | 1 to 2 | 1 | 1.18 |
| +2/+8 | 1 | 1 | 1.5 | 1.19 |
| | 3 | 1 | 1 | |
| | 6 | 1 | 0.8 | 1.18 |
| | 9 | 1 | 1 | |
| | 12 | 1 to 2 | 1 | 1.22 |
| +15/+25 | 1 | 1 | 1 | 1.12 |
| | 3 | 1 | 2 | |
| | 6 | 1 | 4 | 1.49 |
| | 9 | 1 | 10 | |
| | 12 | 1 to 2 | n.i. | 1.28 |
| +37 | 1 | 1 | 10 | 1.27 |

It was observed that the dextran/EDTA formulation prevented the formation of IL2 dimer whatever the temperature studied, particularly at ambient temperature and at 37° C., for which the control formulation without dextran and without EDTA showed a significant dimer formation. Furthermore, it was confirmed that the physical stabilization obtained by the dextran/EDTA formulation also allowed the stability of the biological activity of reduced IL2 to be maintained, whatever the preservation temperature. The stabilization obtained by the process of the invention allowed a prolonged preservation to be achieved of compositions of reduced r-hIL2 containing dextran and EDTA calcium salt, in accordance with the requirements for use as medicaments.

Various modifications of the compositions and method of the invention may be made without departing from the spirit or scope thereof and it is to be understood that the invention is intended to be limited only as defined in the appended claims.

What is claimed is:

1. A stabilized composition comprising an effective amount of non-glycosylated recombinant human IL2 in reduced form, citric acid, mannitol and a preservative effective amount of a mixture of dextran and mono-calcium and disodium ethylenediamine tetraacetate (EDTA calcium salt).

2. A composition of claim 1 wherein the dextran has an average molecular weight of 40,000 to 110,000.

3. A composition of claim 1 wherein the dextran has an average molecular weight of 70,000.

4. A composition of claim 3 with a weight ratio of dextran to IL2 of about 20:1 to about 80:1.

5. A composition of claim 4 wherein the weight ratio is about 40:1.

6. A composition of claim 5 wherein the weight ratio of IL2:citric acid:mannitol:dextran:EDTA calcium salt is about 1:10:50:40:0.01.

7. A composition of claim 1 essentially free of IL2 dimer.

8. A method of stabilizing a composition containing non-glycosylated glycosylated recombinant human IL2 in reduced form, citric acid and mannitol comprising incorporating into said composition an amount of a mixture of dextran and mono-calcium and disodium ethylenediamine tetraacetate (EDTA calcium salt) sufficient to stabilize the composition.

9. The method of claim 8 wherein the dextran has an average molecular weight of 40,000 to 110,000.

10. The method of claim 8 wherein the dextran has an average molecular weight of 70,000.

11. The method of claim 8 with a weight ratio of dextran to IL2 of about 20:1 to about 80:1.

12. The method of claim 8 wherein the weight ratio is about 40:1.

13. The method of claim 8 wherein the weight ratio of IL2:citric acid:mannitol:dextran:EDTA calcium salt is about 1:10:50:40:0.01.

* * * * *